United States Patent [19]
Myers

[11] Patent Number: 5,941,897
[45] Date of Patent: Aug. 24, 1999

[54] ENERGY ACTIVATED FIBRIN PLUG

[76] Inventor: Gene E. Myers, 1310 S. Lakeshore Dr., Sarasota, Fla. 34231

[21] Appl. No.: 08/853,725

[22] Filed: May 9, 1997

[51] Int. Cl.$^6$ .................................................. A61B 17/00
[52] U.S. Cl. .............................. 606/213; 604/93; 604/96; 604/181
[58] Field of Search ................................ 604/93, 96, 181; 606/213

[56] References Cited

U.S. PATENT DOCUMENTS

| | | |
|---|---|---|
| 4,427,650 | 1/1984 | Stroetmann . |
| 5,030,215 | 7/1991 | Morse ..................................... 604/410 |
| 5,213,580 | 5/1993 | Slepian et al. .............................. 623/1 |
| 5,391,183 | 2/1995 | Janzen et al. ............................ 606/213 |
| 5,413,571 | 5/1995 | Katsaros et al. . |
| 5,437,631 | 8/1995 | Janzen et al. .............................. 604/49 |
| 5,486,195 | 1/1996 | Myers ..................................... 606/213 |
| 5,626,601 | 5/1997 | Gershony et al. ....................... 606/194 |
| 5,725,498 | 3/1998 | Janzen et al. .............................. 604/51 |
| 5,810,885 | 9/1998 | Zinger .................................... 606/213 |

FOREIGN PATENT DOCUMENTS

| | | |
|---|---|---|
| 0482350A2 | 4/1992 | European Pat. Off. . |
| WO92/22252 | 12/1992 | WIPO . |

OTHER PUBLICATIONS

Israels, et al., "Development of Antibodies to Bovine and Human Factor V in Two Children After Exposure to Topical Bovine Thrombin", *The Am. Jour. of Pediatric Hematology/Oncology*, 16 (3) :249–54, Aug. 1994.

Banniger, et al., "Fibrin Glue in Surgery: Frequent Development of Inhibitors of Bovine Thrombin & Factor V", *British Journal of Hematology* 85(3): 528–32, Nov. 1993.

Berruyer, et al., "Immunization by Bovine Thrombin Used with Fibrin Glue during Cardiovascular Operations. Development of Thrombin and Factor V Inhibitors", *Journal of Thoracic Cardiovascular Surgery* , 105(5):892–7, May 1993.

Hill–West, et al., "Inhibition of Thrombosis and Intimal Thickening by In Situ Photopolymerization of Thin Hydrogel Barriers", *Nat'l Academy of Science USA*, vol. 91, 5967–71.

Hantgan, et al., "Fibrinogen Structure and Physiology", *Hemostasis and Thrombosis: Basic Principles and Clinical Practice*, Chapter 14, 3rd Edition, pp. 277–300 (1994).

Ichinose, et al., "The Blood Coagulation Factors: Tehir cDNAs, Genes, and Expression", *Hemostasis and Thrombosis: Basic Principles and Clinical Practice*, Chapter 2, 3rd Ed., pp. 19–24 (1994).

*Primary Examiner*—Gary Jackson
*Attorney, Agent, or Firm*—Nikolai, Mersereau & Dietz, P.A.

[57] ABSTRACT

The present invention provides an apparatus and a method for controlled sealant closure, visualization and evaluation of an anterior arteriotomy site in a patient by means of a fiberoptic system in combination with a radiant energy sensitive synthetic human or non-human base sealant. The sealant material undergoes a reaction in which the property of the sealant is converted from liquid to solid or semi-solid, with the reaction being triggered or energized by exposure to radiant energy.

3 Claims, 2 Drawing Sheets

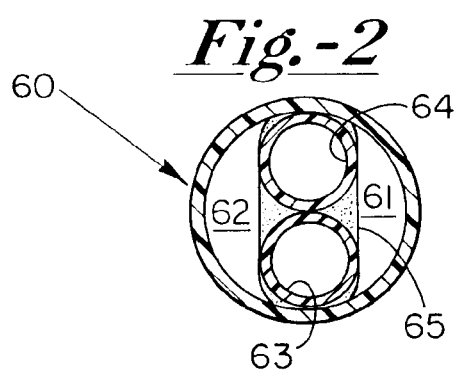
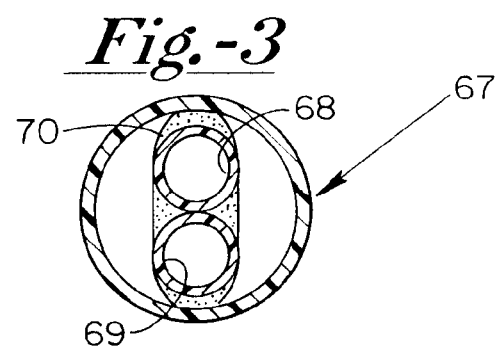
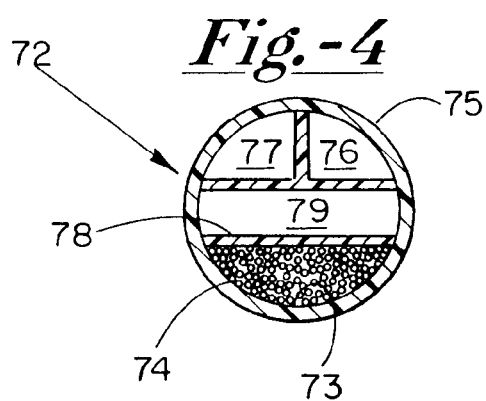
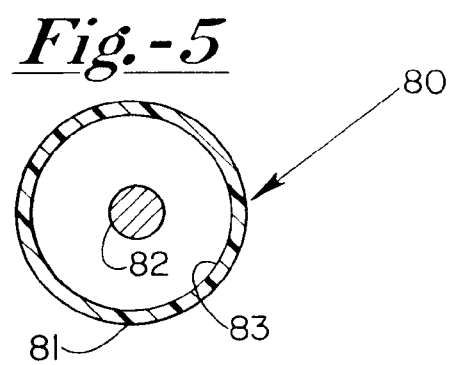
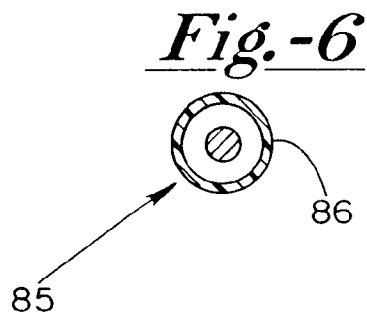

ENERGY ACTIVATED FIBRIN PLUG

CROSS-REFERENCE TO RELATED APPLICATION

The present application constitutes an application for United States Letters Patent to that certain Disclosure Document No. 401417, filed on Jun. 17, 1996, entitled "ENERGY ACTIVATED FIBRIN PLUG" of Gene E. Myers, M.D.

BACKGROUND OF THE INVENTION

The present invention is an improvement over that disclosed and claimed in my U.S. Pat. No. 5,486,195 dated Jan. 23, 1996, the substance of which is incorporated hereinto by reference.

This invention relates to the sealing of a vascular puncture site. In particular, this invention relates to material and apparatus capable of facilitating the rapid sealing of an arterial puncture site using an energy sensitive, naturally occurring or synthetic (or a combination of both) sealant composition. The invention finds particular application to closure of an anterior arteriotomy site in a patient.

During approximately the 1940's, the Seldinger technique of percutaneous entry into a vascular structure by use of a needle and a guidewire technique was introduced to modern medicine and has subsequently become the standard in the medical industry. Prior to Seldinger's discovery of his technique for entry into vascular structures, procedures required an incision through the skin and tissues, commonly followed by an incision into the artery wall.

These earlier techniques had numerous associated problems, such as for example, infection, uncontrolled bleeding, trauma to the tissue and vascular wall, and others. Thus, the advent of the Seldinger technique was widely and rapidly accepted by the medical profession and it became the world standard due to its advantages to both patient and doctor. The patient benefited by less trauma, reduced risk of uncontrolled bleeding and vessel clotting, along with greatly reduced risk to infection. Doctors benefited by the ease of entry and exit in the procedure.

Seldinger's technique does not require suturing the artery puncture site or the skin and adjacent tissue as required in earlier procedures. Over the past 50 years, Seldinger's technique has remained virtually unchanged, its many advantages far outweighing the main or primary disadvantage, namely the sealing of the arterial puncture site. Using Seldinger's technique in order to seal the arterial puncture site, it is necessary to apply strong pressure to compress the arterial wall sufficiently to reduce blood flow and intraluminal pressure to allow initiation of the body's own hemostatic processes. Typically, compression takes between 45 minutes to one hour before closure of the arteriotomy by natural clotting. Thereafter, inactivity with bed rest is required for a period of from 8 to 12 hours to allow the clot to strengthen. The patient often cannot return to normal activity for periods of up to two to three days following arteriotomy procedure.

The medical, social and economic impact of this prolonged recovery period is substantial. In fact, with over three million arteriotomy procedures undertaken annually in just the United States, the prolonged recovery period of Seldinger's technique has an economic impact of billions of dollars incurred through additional hospital stay costs alone. Therefore, a need exists to develop a safe and effective means for effectively and expeditiously sealing the arterial wall following arteriotomy procedures which allows the patient to quickly return to normal activity.

Current procedures to seal the arteriotomy site normally consist of a direct surgical suture closure or the application of sufficient external pressure so as to exceed the fluid pressure existing within the vascular structure, thus eliminating seepage through the arteriotomy site, permitting the body's clotting system sufficient time to form a clot to seal off the arteriotomy site.

New technology emphasizing the application of a non-human, pre-formed collagen plug has demonstrated significant effectiveness. However, the long and short term effects of routinely implanting such foreign materials are of concern and remain unknown.

Additionally, in recognition of the dangers posed when entering the vascular lumen, much emphasis has been placed on developing a delivery system which measures the distance from the skin to the puncture site. In one procedure, a biodegradable suture material anchor is actually sunk through the vascular wall and into the lumen in an attempt to obtain a snug fit of the collagen plug, with the plug being pulled down over a piece of suture towards the arterial puncture site. This step introduces an additional foreign substance into the lumen at the arteriotomy site. Other techniques use a percutaneous technique of closing the arteriotomy site with sutures being introduced from the outside to the inside of the artery. Still another technology uses a similar percutaneous technique but sutures the artery from the inside to the outside.

The main difficulty, however, is that most cardiologists are neither familiar with nor are they comfortable with suturing arteries. This was not the case 20 years ago, but in the past 20 years, suture closure of an arteriotomy site has become rare. Another difficulty arises in that the technologies that try to advance a collagen plug towards the artery, do so without debriding the anterior arterial wall, and thus the plug never contacts the anterior arterial wall surface in juxtaposition to the arteriotomy. Thus, this system or technique permits body seepage to continue to occur between the anterior arteriotomy area and the bottom of the plug when the plug has failed to reach the actual wall surface.

The objective of all these techniques has been to eliminate the 6 to 24 hour bedtime requirement when simple external pressure has been used to obtain closure of the arteriotomy site. Immediate sealing of the arteriotomy site by proper use of a plug technique dramatically facilitates early ambulation of the patient, thus eliminating medical, social and financial costs associated with the above.

In an effort to preserve the effectiveness of the plug technique and to further maximize patient safety, another device and technique was developed permitting debridement of the anterior arterial wall and the use of a sealant such as a fibrin glue. In the device used in this technique, tandem balloons are located such that the distal balloon, when inflated, occludes the intraluminal arteriotomy site. A second external balloon inflates over the anterior arterial wall debriding the tissue and creating a cavity beneath the balloon, permitting the injection of a two-component fibrin glue (beef thrombin) and fibrinogen derived either from cryoprecipitate or autologous fibrinogen. When these two substances come into contact one with the other and additional materials such as calcium and apoprotein are added, a rapidly hardening sealant is formed which attaches to the debrided anterior arterial wall in juxtaposition to the arteriotomy site. As gelling commences, the distal balloon within the arterial lumen is deflated and pulled back through the gelatinous material, with the external balloon being permitted to remain in place until the glue fully hardens and becomes attached to the area adjacent the arteriotomy and within the anterior arteriotomy site. In those situations where anticoagulants have been administered before commencing the procedure and the normal in-vivo clotting mechanisms are altered, this latter device would function to accommodate such a situation. By way of explanation, once the fibrinogen and fibrin have been combined and adhere to the area adjacent to the anterior arteriotomy site, anticlotting agents have no significant effect on the plug.

There are difficulties experienced with the above-described technology and procedure, and certain of them are as follows:

1. One must inject the glue as two separate components so that the injected components do not come into contact, one with the other, so as to "set up" in the lumen through which they are injected.
2. The necessity of keeping the two components separate from one another results in incomplete mixture at the arteriotomy site and significantly reduces the strength and effectiveness of the resultant glue blend.
3. One must carefully coordinate the pullback of a distal balloon through the glue while it is in the process of setting up so as to wait sufficiently long so that the glue becomes sufficiently set and cannot enter the lumen of the artery, and yet not so long that the glue becomes "set up" to the extent that difficulties are created in pulling the balloon through the gelling or gelled substance.
4. There is significant unpredictability to the concentrations of the glue formulations so that the rate at which gelling occurs depends on a number of variables which are difficult to control and/or determine. Among these are the amounts of calcium, apoprotein and other chemical substances released by the disrupted tissues.

Additionally, there are immunological and infectious complications associated with the present FDA-approved glue components (bovine thrombin) and human-pooled cryoprecipitate (the source of fibrinogen) Immunological studies have demonstrated a high incidence (11 of 24 patients) of antibodies to bovine thrombin, resulting in the development of thrombin and factor V inhibitors. The latter is felt to be associated with factor V contaminant in the FDA-approved bovine thrombin. These antibodies may cross-react with human coagulation factors, particularly factor V, resulting in clinical bleeding. Infectious concerns about the FDA-approved source for fibrinogen surround the possible contamination of hepatitis A, B and C and the human immunodeficiency virus (HIV).

To overcome the immunological and infectious concerns, the sealant industry has developed promising new technologies. Pooled human thrombin and fibrinogen can now be treated by a solvent detergent technique, which eliminates the lipid-laden, enveloped viruses including hepatitis B, hepatitis C, and the HIV virus. Pasteurization eliminates hepatitis A. Thus, the immunological and infectious concerns can be eliminated. In addition, novel synthetic, ultraviolet (UV) light sensitive, biogradable polymers such as polycaprolactone have been developed as efficient sealants.

Recognizing that the application of thoroughly mixed sealant in a fine, evenly distributed manner is critical to hemostasis at the arteriotomy site, technologies have recently been developed which render the thrombin inert and energy sensitive, such that the thrombin and fibrinogen can be thoroughly mixed in vitro without reacting until a specific energy source, such as ultraviolet light, visible light, or laser energy is applied.

Therefore, there still exists a need for a method and apparatus to deliver and evaluate a controlled sealing agent to an arteriotomy site.

SUMMARY OF THE INVENTION

Therefore it is a primary object of the present invention to provide an improved method and apparatus for arteriotomy closure, with the apparatus comprising an elongated flexible catheter having a means for evaluating and visualizing the arteriotomy site and a means for delivering an energy-sensitive or energy-responsive sealant to that site to form a fluid-tight seal thereon.

It is a further object of the present invention to provide a means for activating an energy-sensitive or energy-responsive sealant once positioned relative to an arteriotomy site for closure thereof.

Other and further objects of the present invention may become apparent to those skilled in the art upon a study of the following specification, appended claims, and accompanying drawings.

BRIEF DESCRIPTION OF THE DRAWINGS

FIG. 2 is a cross-sectional view of a catheter system usable in accordance with the present invention and including a catheter sleeve together with internally positioned tubes creating lumens for accommodating distal balloon, glue components, and fiberoptics along with venting means;

FIG. 3 is a view of an alternate configuration including a system for transmission of sonic or other energy therethrough;

FIG. 4 is a cross-sectional view of a still further catheter assembly including lumens for transmission of glue, fiberoptics for transmission of radiant energy, a balloon-containing lumen along with a vent;

FIG. 5 is a cross-sectional view taken proximal to the distal balloon; and

FIG. 6 is a cross-sectional view taken distally of the distal balloon.

DESCRIPTION OF THE PREFERRED EMBODIMENT

Figure 1:
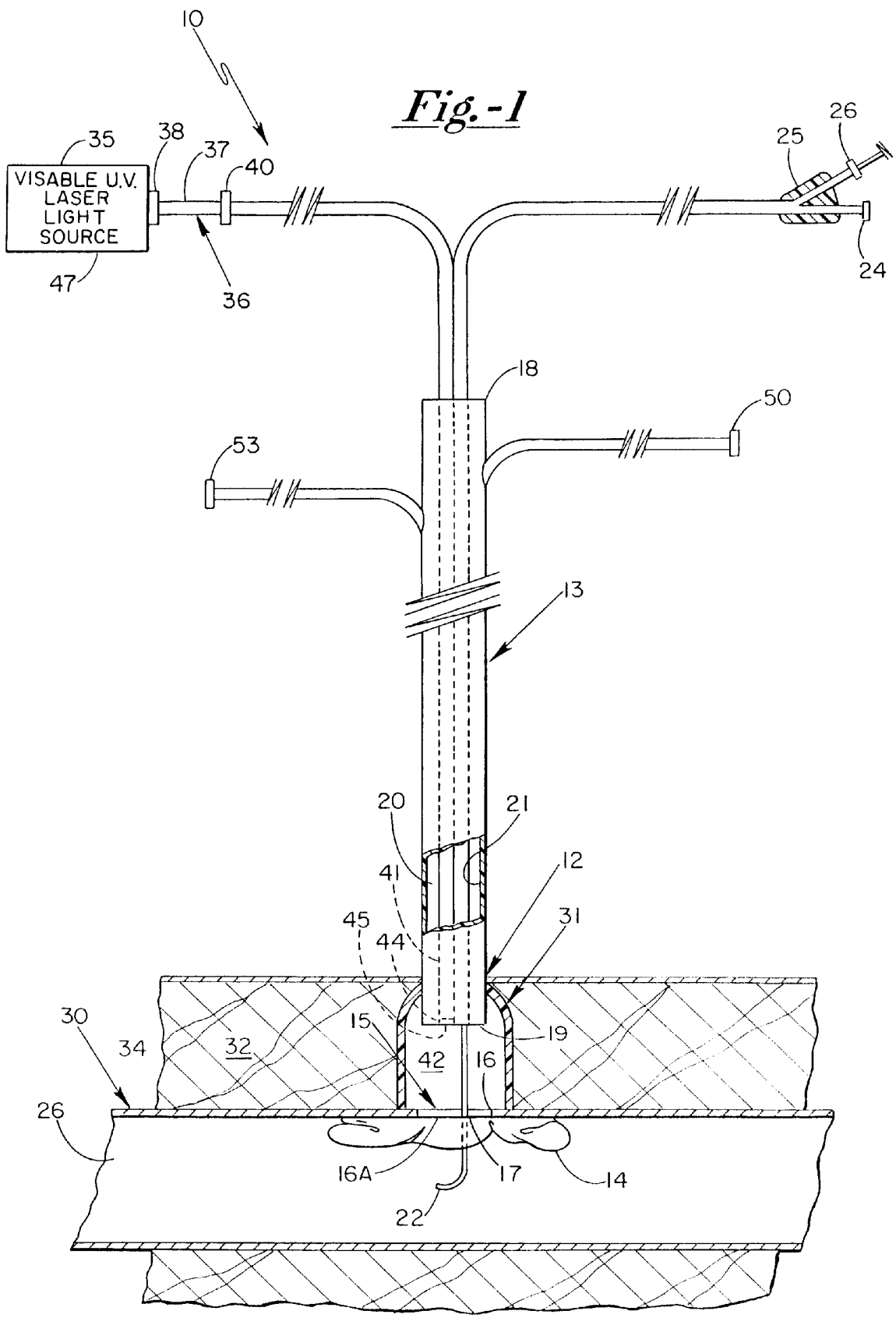
FIG. 1 is a longitudinal cross-section of the debrided arteriotomy site showing the relative locations of the patient's skin, subcutaneous tissue, the walls of the arterial structure, the arterial lumen and direction of blood flow, and wherein one preferred embodiment of the present invention has been inserted into the arterial lumen through the arteriotomy opening.

The present invention may be more readily understood with reference to the following detailed description of certain alternative preferred embodiments and examples and figures included therein.

With attention now being directed to FIGS. 1–6 of the drawings, one preferred embodiment of the arteriotomy closing device is illustrated. The apparatus generally designated 10 for sealing the arteriotomy site shown generally at 12, comprises a first elongated flexible catheter assembly 13, a means such as an occluding balloon 14 for temporarily occluding an intravascular opening shown generally at 15. A delivery means for depositing material to the arteriotomy site illustrated at 16. Energy-responsive sealant material capable of forming a substantially fluid-tight seal of the arteriotomy site 16 is delivered to the site, with the sealant being energized by the delivery of energy such as radiant energy from an appropriate source. Specifically, and preferably, radiant energy derived from a laser source is utilized. Flexible catheter assembly 13 has a proximal end 18, a distal end portion 19, and a hollow shaft 20 with an external surface therebetween. Wall portion 21 includes and defines at least one lumen therewithin. No residual lumen extends distal to the occluding balloon 14. Wire, such as illustrated at 22, extends distal to the end of the balloon 14. The flexible catheter 13 extends substantially the entire length of the first catheter portion of the assembly, or alternatively, distally at least to the area just beyond balloon 14. One or more openings through the external surface of hollow shaft 20 of catheter 13 are located adjacent to the distal end. The proximal end 18 of lumen formed on shaft 20 is the fluid communication or coupler with occluding balloon 14. Catheter 13 may further comprise a collar 25 having at least one port formed therein at 26. Port 26 is connected to a lumen or lumens formed in hollow shaft 20 of catheter 13, particularly at the proximal end 18 such that each port of collar 25, such as port 26 is in fluid communication with one of the lumens of hollow shaft 20 of catheter 13. Furthermore, catheter 13 may include a flexible metal wire extending proximally thereof to an area distal to port 26 and distally beyond the end of catheter 13. The external surface of the wire 22 is normally glued to the internal surface of the catheter.

In the embodiment illustrated in FIG. 1, the closed volume of occluding balloon 14 is positioned in the intravascular space of the patient's artery 30, with balloon 14 being in communication with a first lumen formed in hollow shaft or tube 20 of the catheter 13. Balloon 14 is thereby placed in communication with first balloon port 24 formed on the collar 25. Balloon 14 may be inflated or deflated by fluid or air introduced or removed respectively along lumen in hollow shaft 20 and through balloon port 24 of lumen on shaft 20. When balloon 14 is inflated, the nose end thereof is capable of plugging and temporarily occluding intravascular opening as at 16A of arteriotomy site 16.

As illustrated in FIG. 1, the apparatus utilized to accomplish sealing of arteriotomy 16 may comprise a means generally designated 31 for debriding subcutaneous tissue 32 from the external surface 33 of the anterior arterial wall 34. This debridement may be carried out by methods known in the art and described in U.S. Pat. No. 5,486,195 (Myers et al.) referred to hereinabove. As shown in FIGS. 2–6 herein, the apparatus comprises means for conducting radiant energy from an energy source such as source 35 through a fiberoptic channel such as fiberoptic bundle 36 (FIG. 4) and into the sub-balloon chamber. The fiberoptic bundle 36 has a proximal end 37 with a coupling 38 to the light source. Generally and preferably, a laser source is employed for delivering coherent energy in either the visible or ultraviolet range. Fiberoptic bundle 36 enters port 40 and extends substantially the entire length of catheter 13 with distal end 41 being exposed to the sub-balloon chamber 42. Furthermore, the distal end of fiberoptic bundle 36, as at 44, may be fitted with a diverging or converging lens as at 45. Lens 45, because of limitations of draftsmanship, is not specifically illustrated. Energy source in the form of laser 47 may include, but is not limited to ultraviolet light, visible light, or other form of coherent laser energy.

Additionally, fiberoptic 44 may be coupled to a suitable means to conduct images from the sub-balloon chamber 42 in order to visualize and inspect the arteriotomy site 16A and its nearby contents. Viewing through port 40 and an associated fiberoptic secured in tube 20 may be utilized for this purpose. In an alternate configuration, the energy source could be ultrasonic such that the source would initiate a "set-up" process of the glue, and with the alternate configuration further comprising a means for evaluating the sub-balloon chamber, its contents, and the arteriotomy site.

An alternate preferred embodiment of the present invention provides an apparatus comprised of an elongated, flexible or rigid catheter with sufficient ports to inject energy-sensitive single or multi-component sealant and with additional ports provided as at 50 to introduce or inject a sealant energizer. Also, a ventilation port may be provided at 53. These ports exit distally into a closed chambered space created by debridement of the anterior arterial wall in juxtaposition to the arteriotomy site. The vent port permits evacuation of gas and tissue fluid, permitting the sealant, while in liquid state, to enter the space without forcing fluid into the tissues adjacent the site or through the arteriotomy into the lumen. This elongated catheter includes an additional port having an energy transmitting (fiberoptic or ultrasound) tubing which may also include a converging or diverging lens along with a compatible means to visualize the arteriotomy site and its chambered contents. The energy employed is preferably radiant energy, although other forms of wave energy such as sonic energy with a suitably sensitive sealant may be employed in certain applications. The arrangement is such that energy from an appropriately selected source may be delivered along the channel and into the chamber containing the energy-sensitive or energy-responsive sealant. The energy source may include, but is not limited, to ultraviolet light, visible spectrum of light, or laser energy of various wavelengths. This technique of using inert but energy-sensitive or responsive sealant permits thorough mixing of the components in vitro, injecting them through a single common port into the chamber with energy-activation of the components being undertaken at a specific point in time, thereby achieving precise control of the rate of conversion from the liquid to gel to solid being undertaken as well.

With attention being directed to FIGS. 2–6 of the drawings, FIG. 2 discloses a multi-lumen catheter 60 having a pair of laterally disposed chordal lumens 61 and 62 along with individually defined tubes 63 and 64 each with a bore defining a separate lumen. Tubular elements 63 and 64 may be combined together by suitable joining means such as a bond zone as at 65.

With attention being directed to FIG. 3, an alternate structure to that illustrated in FIG. 2 is illustrated, with this catheter being shown generally at 67, and incorporating a structure with a pair of independent tubular elements 68 and 69 enclosed therewithin. Retention or bonding means are shown at 70 for retaining tubular elements 68 and 69 in position.

With attention being directed to FIG. 4 of the drawings, this figure illustrates a means for incorporating the fiberoptic elements into a multi-lumen catheter. Accordingly, catheter generally designated 72 is provided with a first lumen 73 incorporating a plurality of optical fibers as at 74. Additionally, a "T"-shaped divider is provided within the bore of main catheter tube 75 so as to define individual lumens as at 76 and 77. The spacing between the "T" divider and the chordal divider 78 defines a fourth lumen as at 79.

With attention being directed to FIG. 5 of the drawings, catheter generally designated 80 includes a tubular body 81 enclosing optical fiber assembly 82 therewithin. Lumen 83 is arranged in the annular zone between the outer surface of optical fiber assembly 82 and the inner surface of tube 81. The intended utilization of the optical fiber element 82 will determine the type of fiber to be utilized, be it a single fiber or alternatively a bundle of individual fibers.

FIG. 6 of the drawings illustrates a still further catheter element generally designated 85 which is configured similarly to that of FIG. 5, but utilizes an outer shell or tube 86 which has a diameter sufficiently small so as to enable its introduction into a catheter such as catheters 60, 67, 72 or 80.

EXAMPLE I

The present invention also provides a method of sealing a debrided or non-debrided arteriotomy. In particular, one method of the present invention comprises steps of:

1. Visualizing by visible light, a sub-balloon chamber surrounding an arteriotomy site and its contents;
2. Placing into proper position within the sub-balloon chamber an energy-sensitive single or multi-component synthetic human or non-human sealant;
3. Visually examining the sealant within the arteriotomy site;
4. Delivering light energy from a visible laser source through the fiberoptic conductor and along the channel and into the distally positioned lens to subsequently expose the chambered energy-sensitive sealant to the energy source;
5. Visualizing by visible light the activated reacting sealant through the lens along a video visualization system as the liquid sealant changes from a liquid state to the gel state;
6. Deflating an occlusive distal balloon and withdrawing it to a position proximal to the sub-balloon chamber and into its own canal. This process may be visualized by the lens coupled to the fiberoptic bundle, port and video visualization unit;
7. Continuous on-line visualization of the arteriotomy site via video visualization to evaluate completion of conversion of gelatinous or liquid sealant to a solid;
8. Inspection of the arteriotomy site and chambered solidifying sealant for seepage of blood from the intraluminal area through the sealed arteriotomy and into the sub-chamber zone and adjacent tissues;
9. Deflating the debriding balloon member of the catheter system; and
10. Withdrawing the deflated debriding balloon member from the anterior arteriotomy site through the subcutaneous tissue until external of the skin.

EXAMPLE II

As an alternative, the present invention may be accomplished through the steps of:

1. Placing into proper position within a sub-balloon chamber an ultraviolet energy sensitive, single or multi-component synthetic human or non-human sealant;
2. Delivering ultraviolet energy from a source through fiberoptic bundle into a lens for subsequent exposure of the UV energy to the UV sensitive sealant;
3. Allowing sufficient duration of time until the exposed UV energy-sensitive sealant converts from a liquid state to a gel state;
4. Deflating the occlusion distal balloon and withdrawing it to a position proximal to the sub-balloon chamber and into its canal;
5. Allowing subsequent duration of time until the exposed UV energized gelatinous sealant converts from a gel to a solid. After deflating the debriding balloon member of the catheter and withdrawal of the debriding balloon member from the anterior arteriotomy site through the subcutaneous tissue until external to the skin.

EXAMPLE III

Another alternative method and apparatus of the present invention comprises the steps of:

1. Placing into proper position within the sub-balloon chamber a laser energy sensitive single or multi-component synthetic human or non-human sealant;
2. Delivering a laser energy source through the port into a collar and along the fiberoptic channel and into the lens, and subsequently exposing the chamber to laser energy sensitive sealant to an energy source;
3. Allowing sufficient duration of time until the exposed laser energy sensitive sealant converts from a liquid state to a gel state;
4. Deflating the occlusive distal balloon and withdrawing it to a position proximal to the sub-balloon chamber and into its own canal;
5. Allowing subsequent duration of time until the exposed laser energized gelatinous sealant converts from a gel state to a solid state;
6. Deflating the debriding balloon member of the catheter; and
7. Withdrawing this deflated balloon from the anterior arteriotomy site through the subcutaneous tissue until external to the skin.

Still another alternative apparatus for use in connection with the present invention places a multi-lumen catheter over a wire to an area just above the arteriotomy and without balloon debridement. This alternative apparatus applies UV, visible, or other laser-generated energy to an energy-sensitive sealant delivered and positioned adjacent the arteriotomy with energy being subsequently delivered along a fiberoptic channel.

Still another alternative apparatus to the present invention includes a multi-lumen catheter with a distally positioned debriding balloon catheter. The apparatus is capable of forming a sub-balloon chamber through which a biodegradable occlusive patch is deployed to the intraluminal space for occluding the inferior intraluminal arteriotomy to prevent leakage of the energy-sensitive sealant from the sub-balloon chamber into the lumen of the vessel. In this embodiment, the occlusive patch is biodegradable.

It is contemplated by the present invention that the methods and apparatus may be used to seal an opening formed in any vessel of the body, including, but not limited, to arteries, veins, lymphatics, and the like. The components of the apparatus such as catheters, balloons, and the like can be dimensioned and configured to seal openings in vessels of varying sizes over a variety of clinical applications utilizing the energized sealants as described.

Energy-sensitive biocompatible sealants are commercially available, with one such sealant being identified by the code name "FOCALSEAL", and sold by FocalSeal International Therapeutics Corporation of Lexington, Mass. Other energy-sensitive sealants are, of course, commercially available.

It will be appreciated that the specific examples given herein are for purposes of illustration only and are not to be construed as a limitation upon the scope of the present invention.

What is claimed is:

1. An apparatus for employing in combination with an energy-sensitive sealant for closure of an arteriotomy in a patient and comprising, in combination:

(a) an elongated catheter having a proximal end, distal end, an external surface, a wall portion defining at least one lumen extending substantially the entire length of said catheter, and at least one opening formed therein adjacent the distal end and whereby the proximal end of at least one lumen is in fluid communication with the external surface of said catheter via said opening, and with at least one lumen extending along at least a portion of the length of said catheter whereby only the proximal end is in fluid/air communication with the external surface of said catheter via said opening;

(b) a debriding balloon and a second lumen is provided extending along at least a portion of the length of said catheter whereby said second lumen is in fluid/air communication with said debriding balloon; and (c) a source of radiant energy responsive sealant;

(d) a third lumen means is provided for delivering energy-responsive sealant from said sealant source to the arteriotomy site;

(e) a source of radiant energy; and (f) a fourth lumen for delivering radiant energy from said radiant energy source to the arteriotomy site.

2. The apparatus as defined in claim 1 wherein the radiant energy is light energy.

3. The apparatus as defined in claim 2 wherein the radiant energy is ultraviolet radiation.

* * * * *